United States Patent [19]
Wright

[11] Patent Number: 5,222,986
[45] Date of Patent: Jun. 29, 1993

[54] HAND PROSTHESIS FOR GRASPING LARGE AND SMALL OBJECTS

[76] Inventor: Donald M. Wright, 1517 Elisha, Danville, Ill. 61832

[21] Appl. No.: 825,996

[22] Filed: Jan. 27, 1992

[51] Int. Cl.⁵ .............................................. A61F 2/56
[52] U.S. Cl. ..................................... 623/64; 623/57; 623/63; 294/902
[58] Field of Search ............... 623/63, 64, 57, 62, 623/65; 602/21, 22, 64, ; 294/25, 902, 97

[56] References Cited

U.S. PATENT DOCUMENTS

| | | | |
|---|---|---|---|
| 1,423,296 | 7/1922 | Armstrong | 623/63 X |
| 2,364,313 | 12/1944 | Pecorella | 623/64 |
| 2,885,686 | 5/1959 | Giaimo | 623/65 X |
| 3,438,630 | 4/1969 | Petti | 294/25 |
| 3,631,542 | 1/1972 | Potter | 602/21 X |
| 4,021,866 | 5/1977 | Wasko | 623/59 |
| 4,225,983 | 10/1980 | Radocy et al. | 623/64 X |
| 4,765,320 | 8/1988 | Lindemann et al. | 602/22 |

FOREIGN PATENT DOCUMENTS 0608640 9/1948 United Kingdom ............ 623/57

*Primary Examiner*—Randall L. Green
*Assistant Examiner*—D. Willse
*Attorney, Agent, or Firm*—Roger M. Fitz-Gerald

[57] ABSTRACT

A hand prosthesis utilizing wrist movement and capable of securely grasping both large objects and small objects.

4 Claims, 2 Drawing Sheets

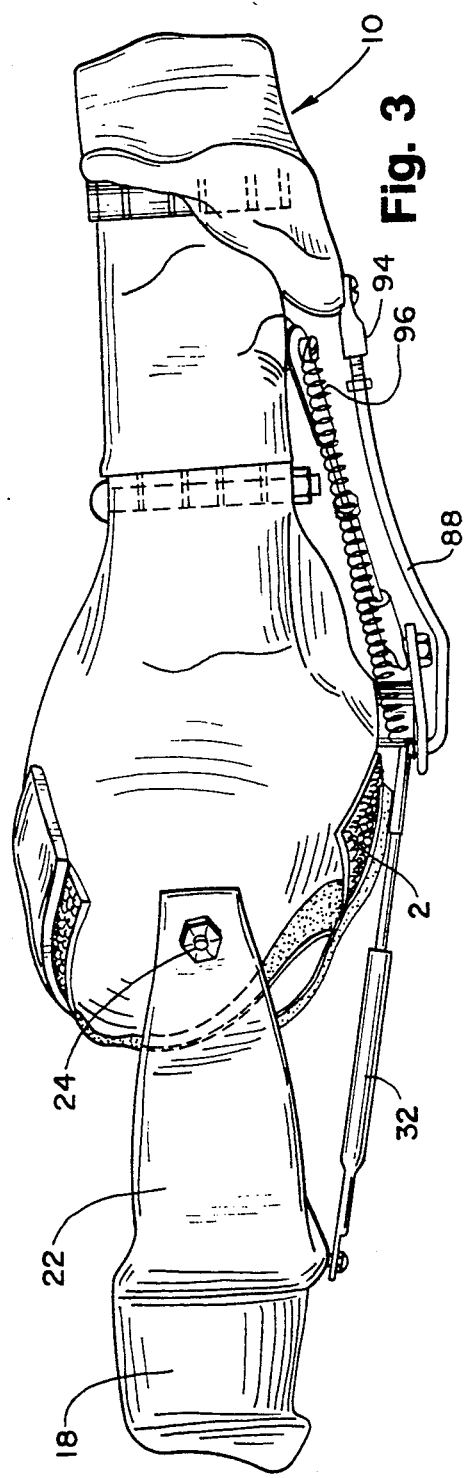
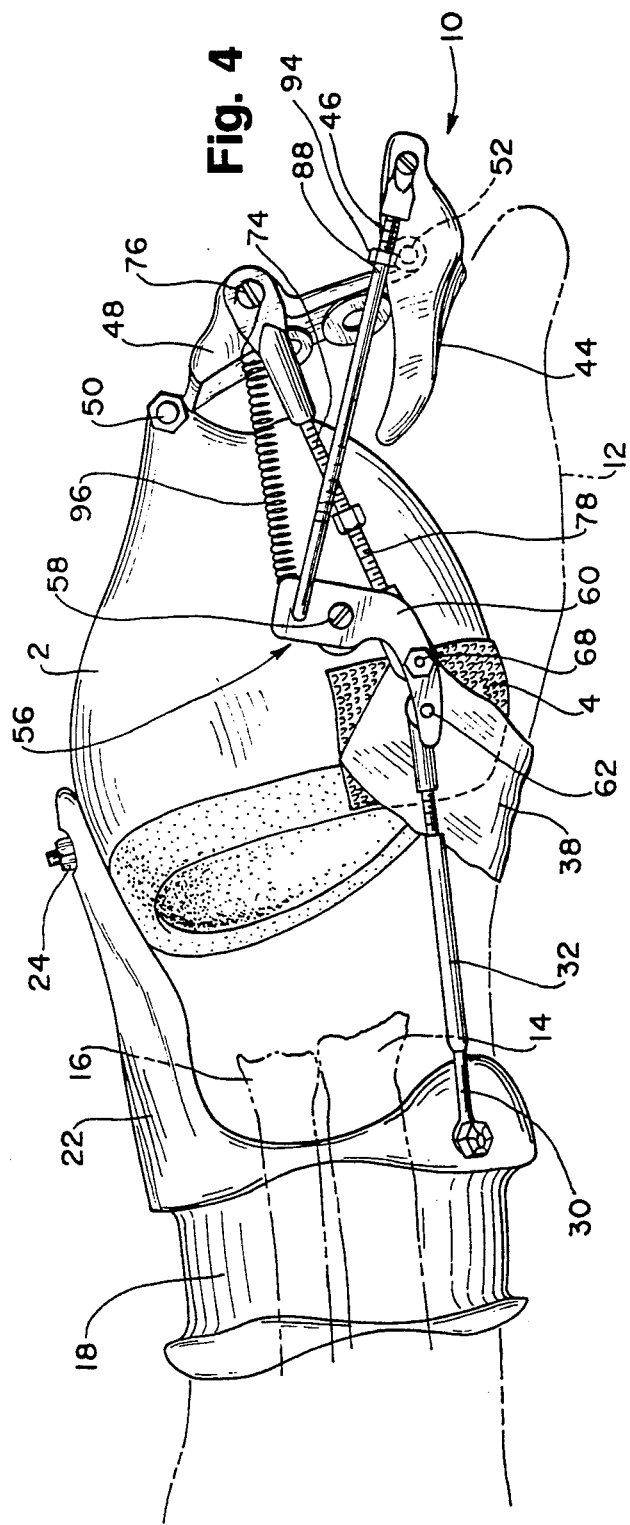

HAND PROSTHESIS FOR GRASPING LARGE AND SMALL OBJECTS

BACKGROUND

The present invention relates to a prosthesis which functionally substitutes for the hand of a person who has had portions of a hand amputated as a result of disease or injury or who because of paralysis of muscles controlling the movement of digits is unable to grasp objects effectively. Generally, such prostheses are in one of two classes—those which are primarily directed toward a cosmetic imitation of a natural hand and those which are primarily directed toward providing the functions of the missing or paralyzed members. The goals of the two classes of prostheses are generally incompatible although many devices have been developed which seek to reconcile these goals.

An example of a device which is primarily cosmetic is shown in U.S. Pat. No. 1,893,714 in which finger elements and thumb elements shaped to imitate flexed fingers and thumb are adapted to fit over the stubs of amputated fingers and thumb. Both elements are secured by a wrist band. The normal movement of the finger and thumb stubs causes similar movement of the artificial elements to provide a crude grasping action which can engage small objects such as a pen or pencil.

Other devices utilize cable and pulley systems to flex multi-jointed artificial finger or finger and thumb elements. These are more functional than the device in U.S. Pat. No. 1,893,714 and the artificial members may cosmetically resemble natural appendages. But one disadvantage of these devices is the lack of durability and strength of the cables and the possibility of breakage or disconnection of the cables. U.S. Pat. No. 4,291,421 shows a hand and forearm prosthesis actuated by cables anchored on the upper arm. U.S. Pat. No. 2,867,819 shows artificial fingers actuated by cables anchored on the wrist for a person whose wrist and thumb is intact. U.S. Pat. No. 2,893,016 and No. 2,553,277 use cables to move paralyzed digits.

Many devices have been proposed to provide a grasping function when a hand has been completely amputated. See, for example, U.S. Pat. No. 1,546,726 and No. 4,016,607, both of which use interacting hooks.

Many devices have also been proposed to provide a grasping function when a portion of the fingers, thumb or metacarpal region remains. U.S. Pat. No. 1,498,029 and No. 3,434,163 both disclose artificial fingers fixedly anchored at the wrist for use with a thumb which remains and is movable to provide a grasping function for small objects. U.S. Pat. No. 2,568,298 discloses articulated artificial fingers which can assume an open or closed relationship with a thumb. This is accomplished using spring loaded levers and a change of position must be initiated by pressure from the individual's intact hand or other object.

U.S. Pat. No. 4,021,866, designed for use where only the wrist joint and finger stubs remain, discloses one plate anchored proximally to or above the wrist and hinged adjacent the wrist to a second plate. Flexing and extension of the wrist joint opens and closes the space between the two plates.

All of these devices have a common functional deficiency. They are adapted to close upon and grasp an object in a narrow range of dimensions. An operating hand prosthesis designed to grasp small objects, such as a needle, pen or pencil or intravenous tubing, is not well adapted to grasping larger articles such as a doorknob, tumbler of liquid, computer mouse, or pieces of furniture or equipment, and the reverse is also true. An intact hand, by contrast, has a range of grasp from the almost dimensionless, the thickness of a hair, to five to seven or more inches.

Most of the devices have an outside or largest range of grasp defined by the distance between the end of the thumb in its extended position and the ends of the artificial fingers in their extended position. In the normal hand a greater range can be obtained by flexing the wrist and fingers posteriorly while maintaining the thumb in extension. The device in U.S. Pat. No. 4,021,866 conceivably could provide a broader range limited only by the length of the grasping plates. However, in this device the hinge produces grasping surfaces which diverge from one another in a "V" shape which is antithetical to secure grasping because the grasping force tends to move the grasped object toward the ends of the plates.

SUMMARY

A hand prosthesis utilizing wrist movement and capable of securely grasping both large objects and small objects.

BRIEF DESCRIPTION OF DRAWINGS

FIG. 3 is a posterior elevational view of the prosthesis as shown in FIG. 2 omitting the body portions.

FIG. 4 is a side elevational view of the prosthesis as shown in FIG. 1 also showing portions of the arm and finger and hand stubs in phantom and looking toward the medial plane.

DETAILED DESCRIPTION

Figure 1:
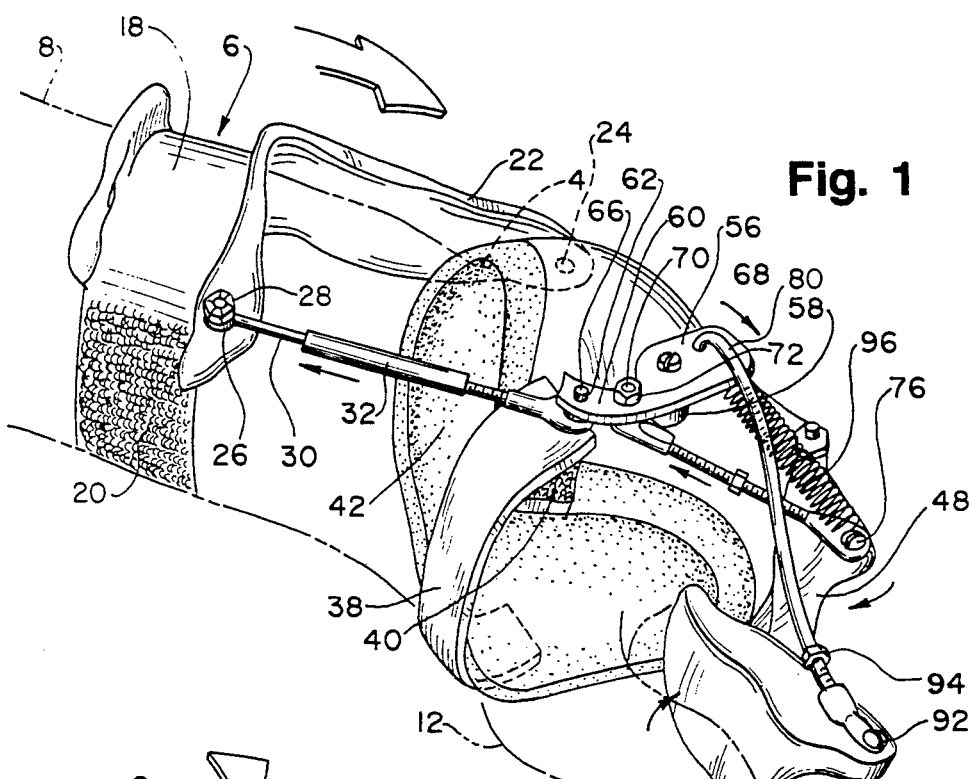
FIG. 1 is a perspective view of a prosthesis in accordance with the invention where the wrist joint is extended, also showing portions of the arm and finger and thumb stubs in phantom.

In the following description and claims, references to parts of the hand and arm are usually made by referring to the bones or skeletal structure. Such references should not be construed to exclude the existence of other related or adjacent structures such as muscles, tendons, ligaments, circulatory or lymphatic organs or structures or the complex structure of the integument or skin. In addition, the drawings show the prosthesis as constructed and used on a left hand but the prosthesis is equally useful on a right hand.

In the description and claims, with reference to the structure of the hand, the term "anterior" is used to refer to structures toward the palm of the hand and "posterior" is used to refer to structures toward the back of the hand. Similarly, "lateral" is used to refer to structures more toward the thumb and "medial" is used to refer to structures more toward the fifth phalange or little finger. This is in accord with the standard anatomical position in which the palms face forward and descriptions thereof, although such conventions may be confusing to the layman because it is the least natural position for the arm and hand in normal use. The term "proximal" is used to refer to structures closer to the elbow. Its opposite is "distal".

With respect to muscle, joint and bone movement, the terms "flexion" and "extension" and derivative terms are used in accordance with standard medical terminology. The wrist joint and metacarpals are flexed when they are rotated posteriorly or rotated anteriorly. In "extension" the metacarpals are more or less in line with the forearm. In use of this prosthesis, posterior flexion of the wrist and metacarpals results in an increase of the grasping range. Anterior flexion of the wrist and metacarpals is not used with this prosthesis. The grasping range is increased by "extension" of the thumb which is "lateral" movement. It is decreased by either abduction, movement toward the fingers, or flexion or opposition if first phalanges remain for this purpose.

A hand prosthesis in accordance with this invention generally includes a socket means or stub socket 2 adapted to receive a portion of a hand including at least some portion of the second through fifth metacarpal or finger bones 4, an anchor means 6 securing the socket to the forearm 8, and a grasping means or gripper member 10 adapted to engage or be engaged by the thumb or a portion thereof 12, namely, at least the first metacarpal or thumb bone and, if they are present, the first proximal phalanx and the first distal phalanx. If necessary or desirable, an extension for the first metacarpal bone may be provided as shown in U.S. Pat. No. 1,893,714. As used herein, the term "thumb" will be used to describe all such individual configurations. The prosthesis is particularly useful where the individual retains some ability to move the thumb either in flexion, abduction or opposition to the position where the missing fingers would be. However, it will become apparent from the description that an individual whose thumb stub is immobile could also utilize the prosthesis by appropriate dimensional adjustment of various elements.

Figure 2:
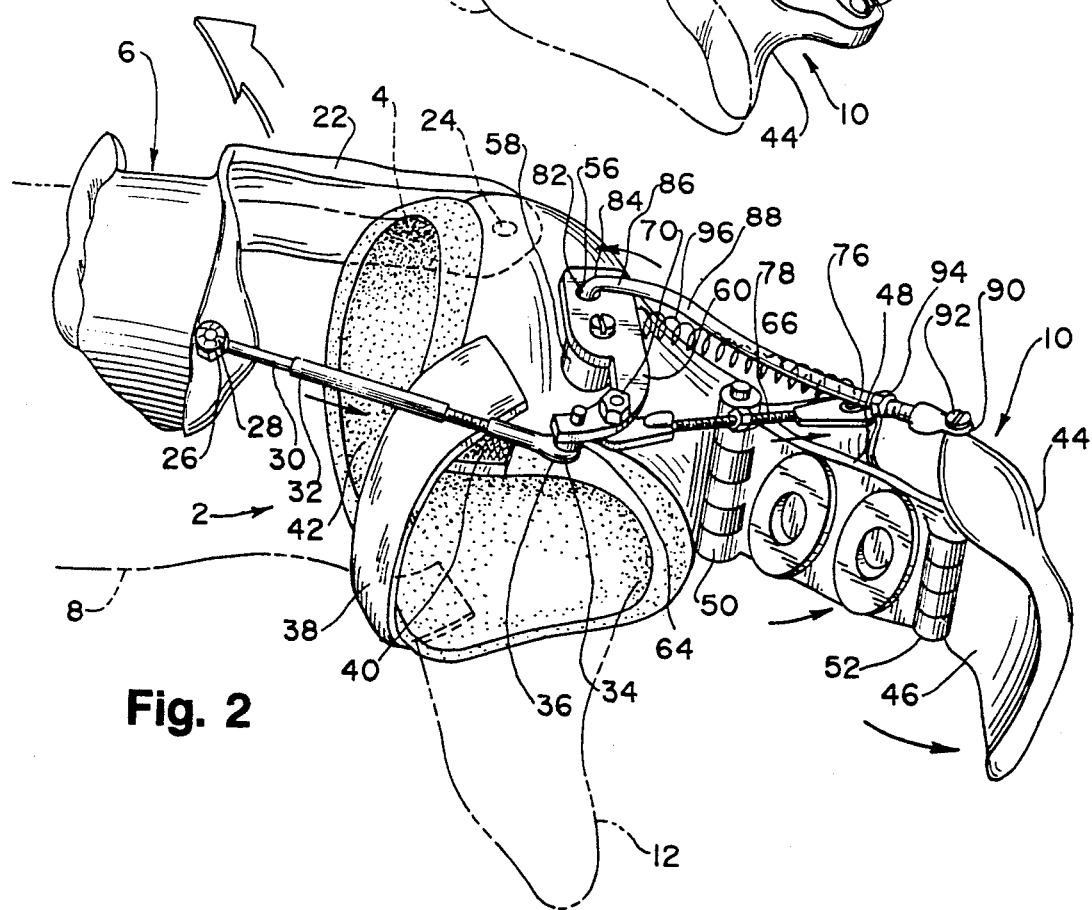
FIG. 2 is a perspective view of the prosthesis where the wrist joint is flexed, also showing portions of the arm and finger and hand stubs in phantom.

The gripper member 10 is adapted to be movable between a first position shown in FIGS. 1 and 4 and a second position shown in FIGS. 2 and 3. In the first position, the gripper 10 is relatively close to the thumb portion 12 and small objects such as a pen, pencil or eating utensil may be grasped by movement of the thumb portion 12 toward the gripper. In the second position, the gripper 10 is further removed from the thumb portion and larger objects such as a tumbler or doorknob may be grasped between the thumb portion 12 and the gripper 10.

The anchor 6 generally engages the forearm in the manner of a wrist watch and band above the head 14 of the radius and the head of the ulna 16, both shown in phantom in FIG. 4. These two bony protuberances provide a blockage to movement of the anchor beyond the distal end of the forearm when, in operation of the prosthesis, forces are exerted pulling the anchor distally toward the hand. As illustrated, the anchor includes a back or posterior portion 18 which is slightly flexible circumferentially to conform to the shape of the posterior side of the forearm and an adjustable portion 20 which can be in the form of a strap with holes and a buckle or a hook and loop or Velcro ® strip to adjust the tightness of fit around the forearm. Alternatively, the posterior portion may be secured to the forearm by a conventional adjustable watchband including a wristwatch. The tightness of fit of such bands assists in securing the anchor against distal movement. The inner surface of the anchor desirably includes a soft material such as felt for the comfort of the user.

The anchor 6 includes or is attached to a distally extending beam 22 which is secured on the medial side of the posterior portion of the anchor and is pivotally connected at 24 to the medial side of the stub socket 2. On the lateral side of the posterior portion of the anchor there is provided a post 26 extending outwardly from the anchor and a post stop 28. Journaled on the post for movement inwardly and outwardly between the anchor and post stop and pivotal movement, if necessary, is one end of a first connecting rod 30. This connecting rod 30 may be adjustable in length, as illustrated by a double ended reverse threaded connector 32 between its two extremities. As shown, the opposite end of connecting rod 30 terminates in a socket 34 forming part of a ball and socket joint 36, although, of course the ball and socket could be reversed in position, connected, as described in detail below to the lateral side of the stub socket 2.

The stub socket 2 is formed to comfortably fit the configuration of the individual's metacarpal stub 4. As illustrated, the proximal edge of the stub socket is generally in the form of a "U", the base of which is adjacent the pivotal attachment of the beam 22. The open end of the "U" shaped edge is closed by a fastener 38. As illustrated, the fastener comprises a Velcro ® strip bridging the open end which mates with other Velcro ® strips 40 on the outside of the stub socket 2 to provide a continuously variable secure fastening of the socket to the finger stub 4. Distally from the "U" shaped edge the stub socket is tapered and formed to fit the actual shape of the individual's finger stub and may be partially closed, as shown, or completely closed.

The socket 2 is a rigid durable molded structure of materials such as those used for conventional plaster casts for immobilizing broken limbs, molded rubber, fiberglass or plastic. The outer surface may be a coating of hardened epoxy to prevent abrasion and an easily cleaned material such as Teflon ®. Conventional plaster casts are used for limited periods of time, unlike this prosthesis, and external abrasion and appearance are not as significant for them. The inner surface of the socket 2 is covered with a soft material 42 such as felt for the comfort of the user.

The gripper 10 is connected to the distal end of the stub socket 2. It is so positioned relative to the socket and thumb, thumb stub or thumb stub extension that it engages the latter in its first position or is engageable by movement of the latter, thus permitting secure grasping of small objects such as a pen or pencil. The gripper 10 is of durable, rigid, easily-cleaned materials providing the same advantages as that of the socket as previously described. It is molded into a shape which provides a small object ripping surface 44 adapted to cooperate with the shape of the individual's thumb, thumb stub or thumb stub extension to grasp small objects when the gripper 10 is in its first position. Most often, the small object gripping surface will be generally concave with some ridges or irregularities to assist in gripping.

The gripper 10 is movable between a first position as shown in FIGS. 1 and 4 suitable for grasping small objects and a second position as shown in FIGS. 2 and 3 for grasping large objects. To facilitate this purpose the gripper is provided with a large object grasping surface 46 on the other side of the gripper from the small object grasping surface 44. As shown, this surface is concave and adapted to grasp one side of a large object such as a tumbler in cooperation with the thumb. Irregularities may also be provided on this surface to assist in grasping. Other shapes could be used to meet the needs of the user.

Means, described in detail below, are provided for moving the grasping means 2 between the first position and the second position. Means are also provided for reorienting the grasping surfaces 44 and 46 more or less concomitantly with said movement.

In a specific embodiment, there is provided a linking arm 48 which is pivotally or hingedly attached at one end 50 thereof to the distal region of the stub socket 2. The other end of the linking member is pivotally or hingedly attached at 52 to the gripper 10 adjacent its large object grasping surface 46. Distally directed force applied to the linking member 48 rotates it around hinge 50 and moves gripper 10 distally and further away from thumb 12 toward the second position. Gripper 10 is constrained at its distal end from moving in complete consonance with the distal end of linking member 48 and, as shown and described below, is forced to move in the opposite direction and, therefore, rotates about hinge 52, bringing the large object grasping surface 46 in opposition to the thumb. Upon completion of this movement the large object grasping surface 46 and the inner surface of the linking member 48 are both in a position to assist in grasping a large object. Suitable surface coverings may be provided on both surfaces with irregular or frictional characteristics to aid in secure grasping.

As illustrated, the distally directed force on linking member 48 is provided by mechanisms which will now be described in detail and which are actuated by flexion of the radiocarpal or wrist joint 54.

The central structure of such mechanisms is a pivot arm 56 mounted on a pivot 58 on the posterior and lateral region of the stub socket 2. As illustrated, the pivot arm is "L" shaped but other shapes and dimensions are usable customized to each user. One arm 60 of pivot arm 56 includes a first pivot hole 62 through which extends pivot post 64. One (as shown) or two post stops 66 may be provided to prevent disengagement of post 64 from arm 60. An end of post 64 is connected to the ball and socket joint 36 on the end of first connecting rod 30. Of course, it would be routine to reverse the ball and socket connections or the pivot hole and post.

Also on arm 60 are a second pivot hole 68, pivot post 70 and post stop or stops 72 which are closer to pivot 58 and more distally located than pivot hole 62. This second pivot post 70 is journaled adjacent the end of second connecting rod 74. The opposite end of second connecting rod 74 is journaled in pivot post 76 on linking member 48 between its two ends. Second connecting rod 74, like first connecting rod 30, may be adjustable in length using connector 78. Once again, the relative connections of pivot elements could be reversed.

On opposite arm 80 of pivot arm 56, third pivot hole 82, pivot post 84 and pivot stops 86, if necessary, are provided. These may be as shown or reversed in position. Third pivot post 84 journals third connecting rod 88, the opposite end of which is pivotally connected adjacent the end of the gripper 10 at pivot post 90 with stop 92, which is more distal than the hinge attachment 52 between the linking member 48 and gripper 10. The third connecting rod may also be adjustable in length with connector 94.

Restoring means, shown as a spring 96 in tension extends between third pivot post 84 on pivot arm 80 and pivot post 76 on linking member 48. Restoring means 96 tends to force gripper 10 closer to thumb 12 and facilitate grasping of larger objects.

In describing the operation of the prosthesis, the reference point will be the forearm on which the anchor is mounted and it will be considered to be fixed. The conventional anatomical position and directions in relation thereto will continue to be employed for consistency with the prior description. Note that these conventions are contrary to the perceptions of most individuals concerned with grasping objects. In most grasping, the posterior of the hand or "the back of the hand" is most forward in relation to the body. Similarly, the thumb, anatomically described as more lateral than the fingers, is usually closer to the median plane of the body than are the fingers.

In operation, the hand stub is extended as shown in FIGS. 1 and 4 and the muscles controlling the stub are relaxed. The forearm, anchor and stub socket are generally aligned with one another parallel to a distally extending axis. The gripper has its small object grasping surface in opposition to the thumb and grasping of small objects occurs either by the predetermined spacing of the surface and thumb or by movement of the thumb toward the surface.

If the user wishes to grasp a larger object, he or she flexes the wrist muscles and wrist joint posteriorly. This rotates the remaining metacarpals posteriorly and stub socket 2 posteriorly around anchor beam pivot 24. As this occurs, one end of first connecting rod 30 rides along post 26. The distal end of first connecting rod 30, riding in the ball and socket joint, maintains pivot arm 56 in the same position relative to the anchor, but in effect rotates pivot arm 56 in relation to stub socket 2. Rotation of pivot arm 56 counterclockwise, as shown in the drawings, through second connecting rod 74 rotates linking member 48 around hinge 50 and moves gripper 10 distally and further from the thumb. Arm 80 of pivot arm 56 moves proximally at the same time. Since arm 80 is connected through third connecting rod 88 to the distal end of gripper 10, the gripper rotates about hinge 52 to present its large object grasping surface 46 to the thumb, all as shown in FIG. 2.

As previously noted, in order to provide more secure grasping action in the second position, a restoring force is provided between arm 80 of pivot arm 56 and linking member 48, which also affects gripper 10. As illustrated, there is a spring 96 in tension anchored between pivot post 76 on arm 80 of pivot arm 56 and pivot post 76 on linking member 48 to provide this function. The restoring force provided, as shown, by spring 96 insures a secure grasp of larger objects.

Thus, a hand prosthesis is provided which facilitates grasping of both large and small objects in closer imitation of the natural function of an unimpaired hand than any prior devices known to the applicant.

Various changes and modifications of the prosthesis, including some which would enhance its cosmetic appearance, will be apparent to those skilled in the art, all of which will fall within the scope of the following claims.

What is claimed is:

1. A hand prosthesis for an individual retaining at least some of the first metacarpal structure, at least some of the second through fifth metacarpal structures, and the capability of movement of the remainder of said second through fifth metacarpal structures between an extended position and a flexed position, comprising:

a. anchor means for securing the prosthesis to the arm of the individual;
b. socket means for receiving therein and engaging said second through fifth metacarpal structures;
c. grasping means connected to said socket means for grasping objects in cooperation with said first metacarpal structure; said grasping means being pivotally movable with respect to said socket means in response to movement of said second through fifth metacarpal structures between a first position for grasping small objects and a second position for grasping large objects;
d. means rigidly connected to said anchor means and pivotally connected to said socket means whereby said socket means is pivotable in relation to said anchor means;
e. a pivot arm pivotable with respect to said socket means;
f. a first connecting rod movably attached to said anchor means and pivotally attached to said pivot arm;
g. a second connecting rod pivotally attached to said pivot arm and operatively connected to said grasping means whereby movement of said socket means causes movement of said grasping means; and
h. a linking member pivotally connected to said socket means and pivotally connected to said grasping means, said second connecting rod being operatively connected to said grasping means through said linking member between the pivotal connection of said linking member to said socket means and the pivotal connection of said linking member to said grasping means.

2. A hand prosthesis in accordance with claim 1 including a third connecting rod pivotally connected to said pivot arm and pivotally connected to said grasping means.

3. A hand prosthesis in accordance with claim 2 including a restoring means connected between said second connecting rod and said third connecting rod, said means providing resistance to movement of said grasping means to its second position and thereby providing a grasping force for an object.

4. A hand prosthesis in accordance with claim 2 wherein at least one of said connecting rods is adjustable in length.

* * * * *